(12) United States Patent
Knighton et al.

(10) Patent No.: US 6,511,494 B1
(45) Date of Patent: Jan. 28, 2003

(54) VEIN HARVESTING SYSTEM AND METHOD

(75) Inventors: David R. Knighton, Minneapolis, MN (US); Vance D. Fiegel, New Brighton, MN (US)

(73) Assignee: Embro Corporation, St. Louis Park, MN (US)

( * ) Notice: Subject to any disclaimer, the term of this patent is extended or adjusted under 35 U.S.C. 154(b) by 0 days.

(21) Appl. No.: 09/715,665

(22) Filed: Nov. 17, 2000

(51) Int. Cl.$^7$ .............................................. A61B 17/00
(52) U.S. Cl. .................................................... 606/190
(58) Field of Search ........................... 606/1, 114, 159, 606/169, 170, 190, 191, 194, 195

(56) References Cited

U.S. PATENT DOCUMENTS

| | | |
|---|---|---|
| 1,867,624 A | 7/1932 | Hoffman |
| 2,001,169 A | 5/1935 | Wallace |
| 2,011,169 A | 8/1935 | Wappler |
| 2,028,635 A | 1/1936 | Wappler |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,856,016 A | 12/1974 | Davis |
| 3,882,854 A | 5/1975 | Hulka et al. |
| 3,934,115 A | 1/1976 | Peterson |
| 4,038,987 A | 8/1977 | Komiya |
| 4,362,160 A | 12/1982 | Hiltebrandt |
| 4,440,170 A | 4/1984 | Golden et al. |
| 4,556,058 A | 12/1985 | Green |
| 4,768,508 A | 9/1988 | Chin et al. |
| 4,793,346 A | 12/1988 | Mindich |
| 5,037,433 A | 8/1991 | Wilk et al. |
| 5,284,478 A | 2/1994 | Nobles et al. |
| 5,373,840 A * | 12/1994 | Knighton ..................... 608/157 |
| 5,425,355 A | 6/1995 | Kulick |
| 5,447,513 A | 9/1995 | Davison et al. |
| 5,549,637 A | 8/1996 | Crainich |
| 5,772,576 A | 6/1998 | Knighton et al. |
| RE36,043 E | 1/1999 | Knighton |
| 6,059,802 A * | 5/2000 | Ginn ........................... 606/159 |
| 6,071,232 A | 6/2000 | Knighton et al. |

FOREIGN PATENT DOCUMENTS

| | | |
|---|---|---|
| DE | 39 42 589 A1 | 7/1991 |
| GB | 2 082 456 A | 3/1982 |
| GB | 2 195 540 A | 4/1988 |
| SU | 112367 | 4/1957 |
| SU | 510235 | 5/1976 |
| SU | 1371689 A1 | 3/1986 |

OTHER PUBLICATIONS

DeLaria et al., "Leg Wound Complications Associated with Coronary Revascularization," *J. Thorac. Cardiovasc. Surg.*, 81:403–407 (1981).

(List continued on next page.)

*Primary Examiner*—David O. Reip
(74) *Attorney, Agent, or Firm*—Popovich & Wiles, P.A.

(57) ABSTRACT

A system for harvesting a section of a blood vessel from a patient's body for further use. The system includes a housing and a removable lower portion that is inserted into an incision to create a workspace for the insertion of tools used to harvest the blood vessel. A multi-lumen body portion is used with various tools to dissect the vein and to protect the vein from any damage during the harvesting procedure. The system can remove a section of the saphenous vein for use in coronary bypass surgery.

6 Claims, 5 Drawing Sheets

OTHER PUBLICATIONS

Dimitri et al., "A Quick and Atraumatic Method of Autologous Vein Harvesting Using the Subcutaneous Extraluminal Dissector," *J. Cardiovasc. Surg.*, 28:103–111 (1987).

Hauer et al., "Endoscopic Subfacial Discission of Perforating Veins," *Surgical Endosc.*, 2:5–12 (1988).

"Incision Decision", Atrium Medical Corporation advertisement, appearing in *J. Thorac. Cardiovasc. Surg.*, 83(4) (1982).

Meldrum–Hanna et al., "Long Saphaneous Vein Harvesting," *J. Surg.*, 56:923–924 (1986).

Moazami et al., "Minimally Invasive Greater Saphenous Vein Harvesting for Coronary Artery Bypass Surgery," *Surgical Rounds*, pp. 94–98 (Mar. 1997).

Rashid et al., "Subcutaneous Technique for Saphenous Vein Harvest," *Ann. Thorac. Surg.*, 37(2):169–170 (1984).

"Saphenous Vein Grafts are No. 1. Period.," Atrium Medical Corporation advertisement, appearing in *J. Thorac. Cardiovasc. Surg.*, 81(6) (1981).

Wheatley, D.J., ed., *Surgery of Coronary Artery Disease*, C.V. Mosby Co., pp. 348–349, 374–375.

Commonly assigned, co–pending U.S. Ser. No. 09/715,382, filed Nov. 17, 2000.

* cited by examiner

VEIN HARVESTING SYSTEM AND METHOD

FIELD OF THE INVENTION

This invention relates to a system for harvesting a generally cylindrical shaped tissue structure from the body of a patient. More particularly, the invention is directed to a system for harvesting a section of a blood vessel from a patient.

BACKGROUND OF THE INVENTION

In certain circumstances it is desirable to remove sections of tubular tissue structure from a patient's body. Such tissue may be used in another part of the patient's body, may be transplanted into a second patient's body or may be discarded. As used herein, the term "tubular tissue structure" includes blood vessels, tendons, bile ducts and any other similar tissue formation which is generally tubular in structure and capable of being separated from surrounding tissue. Although the invention herein will be discussed in terms of harvesting blood vessels it should be understood that the apparatus and method described are equally applicable to harvesting other tubular tissue structures from a human or animal body.

Vein harvesting is commonly done in connection with coronary artery bypass surgery. The saphenous vein is a subcutaneous vein which is often used for coronary artery bypass grafting, infra-inguinal bypass grafting and vein-vein bypass grafting. Other veins may also be used including the mammary vessel and the lessor saphenous vein. Previously, it has been necessary to make an incision along the full length of the vein section to be removed. The vein is then freed by severing and ligating the branches of the vein, after which the section of the vein can be removed from the patient. The full length incision must then be closed, for example by suturing or stapling. Obviously, the harvesting of the vein in this manner leaves disfiguring scars which are cosmetically undesirable. Additionally, the large incision creates a risk of infection to the patient and may not heal properly, especially with those patients who have poor circulation in their extremities. Such an incision may create a chronic wound.

Devices for harvesting a section of a blood vessel without creating a full-length incision have been suggested. U.S. Pat. No. 4,793,346 (Mindich) discloses a device for harvesting a section of a blood vessel by making only small incisions at opposite ends of the blood vessel section. The device includes a guide rod which fits inside the vein section and a tube having an inner diameter slightly larger than the outer diameter of the vein section to be harvested. The tube has one or more knife blades at the leading edge which are connected to an electrical supply. The vein section is removed by making the incision sufficiently deep so as to expose the ends of the blood vessel to be harvested. The blood vessel is cut to expose one end, the guide rod is inserted inside the blood vessel section, and the tube is placed over the end of the blood vessel section to be removed. The tube is then pushed along the blood vessel (into the patient) while rotating the tube to sever the branches of the blood vessel with the knife blade mounted at the leading edge of the tube. Electrical current is supplied to the knife blades to heat the blades and thereby cauterize the ends of the severed branches of the blood vessel. The procedure is continued until the tube has reached the second of the two incisions. The blood vessel is exposed and cut from the patient at the second incision. The tube is then removed from the patient with the blood vessel section inside the tube. The blood vessel section is then removed from the tube for further treatment and used as desired.

UK Patent No. GB 20 82 459A discloses a device for harvesting a section of a blood vessel similar to that disclosed in the Mindich patent. Again, two incisions are made, one at each end of the blood vessel section to be harvested. A guide rod is inserted into the blood vessel section through one of the incisions and a tube having a cutting element having a cutting tool at its operative end is passed over the blood vessel section and guide rod assembly. The tube is rotated as it passes over the blood vessel section to sever the connecting branches. After the tube has passed the entire length of the blood vessel section, the section is cut away through the second incision and the tube is removed from the patient with the harvested section inside the tube.

Blood vessel harvesting devices of this type have certain distinct disadvantages. While they eliminate the need for a full-length incision to remove the blood vessel segment, two incisions, one at each end of the segment to be harvested, are required in order to remove the blood vessel segment. For patients likely to develop chronic wounds, each additional incision increases the risk to the patient, and it is desirable to keep such incisions as close to the patient's trunk as possible and to minimize the number and size of such incisions. Additionally, such devices are unable to adequately close off several branches of the blood vessel and thus are unable to adequately control bleeding. As a result, the patient suffers greater blood loss than is necessary. These prior devices may also remove more tissue than is necessary because the size of the cutting device is not readily adaptable to the changes in the size of the blood vessel.

In U.S. Pat. No. Re 36,043 (Knighton), an improved device and method for vein removal is disclosed which solve some of the problems associated with the use of prior art devices. Knighton discloses an endoscope having a lumen extending longitudinally through the scope body. The endoscope includes means for viewing an area adjacent the distal end of the lumen. The lumen has a lateral dimension large enough to accommodate the blood vessel being harvested and at least one tool for use in harvesting the blood vessel. A first end of the blood vessel section to be harvested is exposed through an incision in the patient's body. A dissecting tool and a gripping tool are inserted through the lumen of the endoscope and used to dissect the blood vessel away from the surrounding connective tissue of the patient's body. Additional tools are provided for use through the lumen of the endoscope to remove body fluids and coagulate bleeding tissue, to ligate and sever side branches from the blood vessel to be harvested, and to ligate and sever a distal end of the blood vessel to be harvested when a desired length of blood vessel has been dissected. Only a small incision in the patient's body is necessary to harvest a relatively long length of blood vessel in a precise and controlled manner using this device and procedure.

U.S. Pat. No. 5,772,576 (Knighton et al.) also describes a device and method for vein removal. The device has one or more lumens extending through a body portion. One lumen is sized to accommodate a blood vessel and at least one tool for use in removing the vessel. The device may also include viewing means so that the operator may remotely view an area adjacent the distal end of the body portion. The device protects the vessel being removed from damage by the tools used in the procedure, which is critical since the blood vessel is destined for reuse (as in arterial bypass). In addition, a single operator can use the device.

However, there is still room for improvement in current vein harvesting devices. It is difficult to see the vein to be harvested, especially near the distal end, even with the use of optical fiber devices. Moreover, it can be difficult to position the tools needed to harvest a vein in a fast and efficient manner and minimize damage to vein and to the patient. Thus a need in the art remains for a convenient method that would effectively harvest a vein without causing any damage to it.

SUMMARY OF THE INVENTION

This invention is a system for the harvesting of a blood vessel. The system comprises a housing having a removable lower portion. In a preferred embodiment, the housing is configured to contain a body portion having at least one lumen. In a more preferred embodiment, the housing is configured to contain a multi-lumen body portion. Various tools are used in conjunction with the housing and the body portion for removal of a blood vessel.

In one aspect the invention is a method of removing a section of a generally cylindrical tissue structure from the body of a human or animal. The method includes providing a device having a first portion and a second portion, the first and second portions defining a working space therebetween, the second portion being movable with respect to the first portion; exposing a proximal end of the tissue structure section to be harvested through an incision in the body; inserting the device through the incision such that the second portion is positioned between the first portion and the tissue structure; moving the second portion with respect to the first portion to expose the working space between the first portion and the tissue structure; inserting at least one tool through the incision into the working space; dissecting the tissue structure away from surrounding tissue with the at least one tool; cutting a proximal end of the tissue structure section; cutting a distal end of the tissue structure section; and removing the tissue structure section through the incision.

The method may include providing a device wherein the first portion has a non-planar shape and the second portion is substantially planar, wherein the second portion is slidably engaged to the second portion and wherein the step of moving the second portion with respect to the first portion includes sliding the second portion out of engagement with the first portion.

In another aspect the invention is a system for removing a generally cylindrical tissue structure from a human or animal body. The system includes a device having an elongate nonplanar housing defining a longitudinal axis; a movable portion configured to be movable with respect to the housing from an engaged position where an at least partially enclosed working space is defined between the housing and the movable portion and a working position where the working space is exposed, the housing and movable portion being sized to be insertable through the incision and positioned adjacent the tissue structure; and at least one tool used in removing the tissue structure, the tool having a distal operative tip and being sized to be accommodated within the working space. The system may further comprise an elongate element having a first lumen sized for accommodating the tissue structure and a second lumen sized for accommodating at least one tool.

In one aspect the invention is a method of removing a generally cylindrical tissue structure from the body of a human or animal. The method comprises providing a means for creating a working space; exposing a proximal end of the tissue structure to be harvested through an incision in the body; inserting the means for creating a working space through the incision adjacent the tissue structure section; manipulating the means for creating a working space to form a working space adjacent the tissue structure section; inserting at least one tool through the incision into the working space between the tissue structure section and the means for creating a working space; dissecting the tissue structure away from surrounding tissue with the at least one tool; cutting a proximal end of the tissue structure section; cutting a distal end of the tissue structure section; and removing the tissue structure section through the incision. The method may further comprise providing an elongate element having first and second lumens and inserting a proximal end of the tissue structure section through the first lumen of the elongate device. Further, the method may comprise providing a substantially cylindrical dissection tool within the first lumen of the elongate member, the dissection tool having a third lumen, inserting a proximal end of the tissue structure section through the third lumen of the dissection tool, providing a cutting tool, and inserting the cutting tool through the second lumen of the elongate element.

In a further aspect the invention is a system for removing a generally cylindrical tissue structure from a lumen or animal body. The system comprises means for creating a working space adjacent the tissue structure in the body, the means being sized to be insertable into the body adjacent the tissue structure through an incision in the body, and at least one tool used in removing the tissue structure, the tool being sized to be accommodated within the working space.

The system may further comprise an elongate element having a first lumen sized for accommodating the tissue structure and a second lumen sized for accommodating at least one tool.

In another aspect the invention is a method for creating a working space for at least one tool over a generally cylindrical tissue structure in a human or animal body. The method comprises providing a device having a first portion and a second portion, the first and second portions defining a working space therebetween, the second portion being movable with respect to the first portion; making an incision in the body above the tissue structure; inserting the device through the incision such that the second portion is positioned between the first portion and the tissue structure; moving the second portion with respect to the first portion to expose the working space between the first portion and the tissue structure; and inserting the at least one tool through the incision into the working space.

In a further aspect the invention is a device for insertion through an incision for creating a working space for at least one tool adjacent a generally cylindrical tissue structure in a human or animal body. The device comprises an elongate nonplanar housing defining a longitudinal axis; and a movable portion configured to be movable with respect to the housing from an engaged position where an at least partially enclosed working space is defined between the housing and the movable portion and a working position where the working space is exposed, the housing and movable portion being sized to be insertable through the incision and positioned adjacent the tissue structure.

BRIEF DESCRIPTION OF THE DRAWINGS

Aspects of the present invention will be appreciated with reference to the description of the invention when read in conjunction with the accompanying drawings.

DETAILED DESCRIPTION OF THE PREFERRED EMBODIMENTS

The present invention is a system for harvesting a section of a vessel from a patient's body for use in another part of a patient's body or for transplanting into a second patient's body. For example, a section of the saphenous vein may be removed for use in coronary bypass surgery. The saphenous vein travels along the medial side of the foot, leg, and thigh, where it joins with the femoral vein near the groin.

The terms "distal" and "proximal" as used in this specification refer to the method use of the device. "Proximal" refers to a location closer to the physician and "distal" refers to a location farther from the physician. "Upper" and "lower" are terms that refer to an orientation with respect to the use of the device, that is, relative to the physician.

Figure 1A:
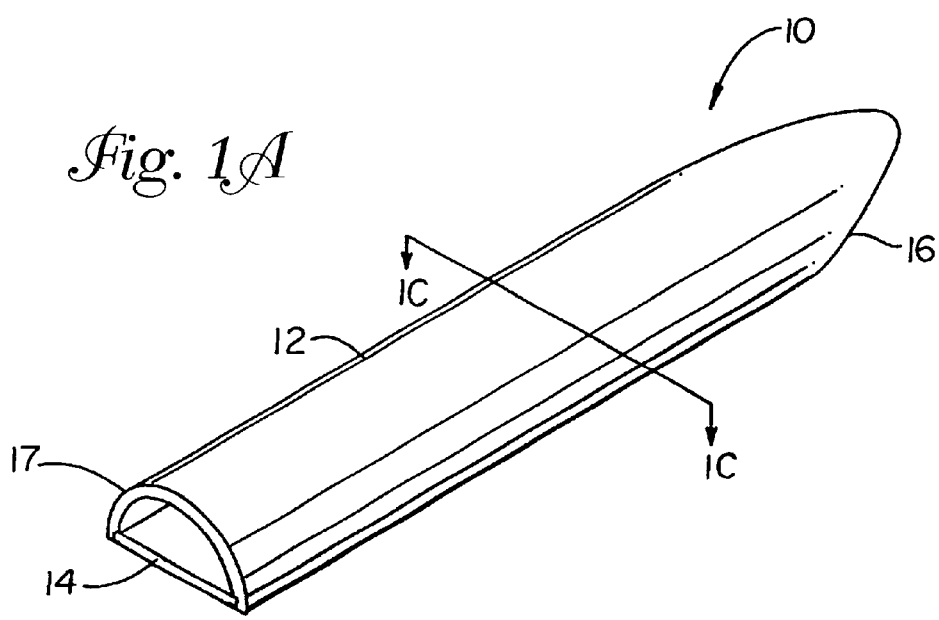
FIG. 1A is a perspective view of the device of the present invention.
Figure 1B:
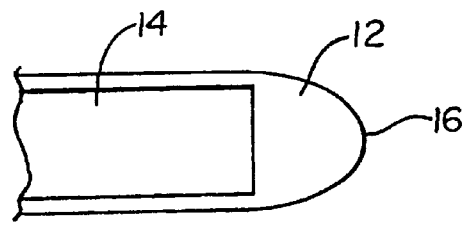
FIG. 1B is a partial bottom view of the distal end of the device of FIG. 1A.
Figure 1C:
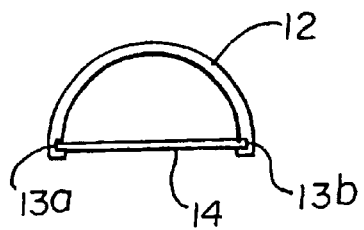
FIG. 1C a transverse cross-sectional view of the device of FIG. 1A along line 1—1.
Figure 6:
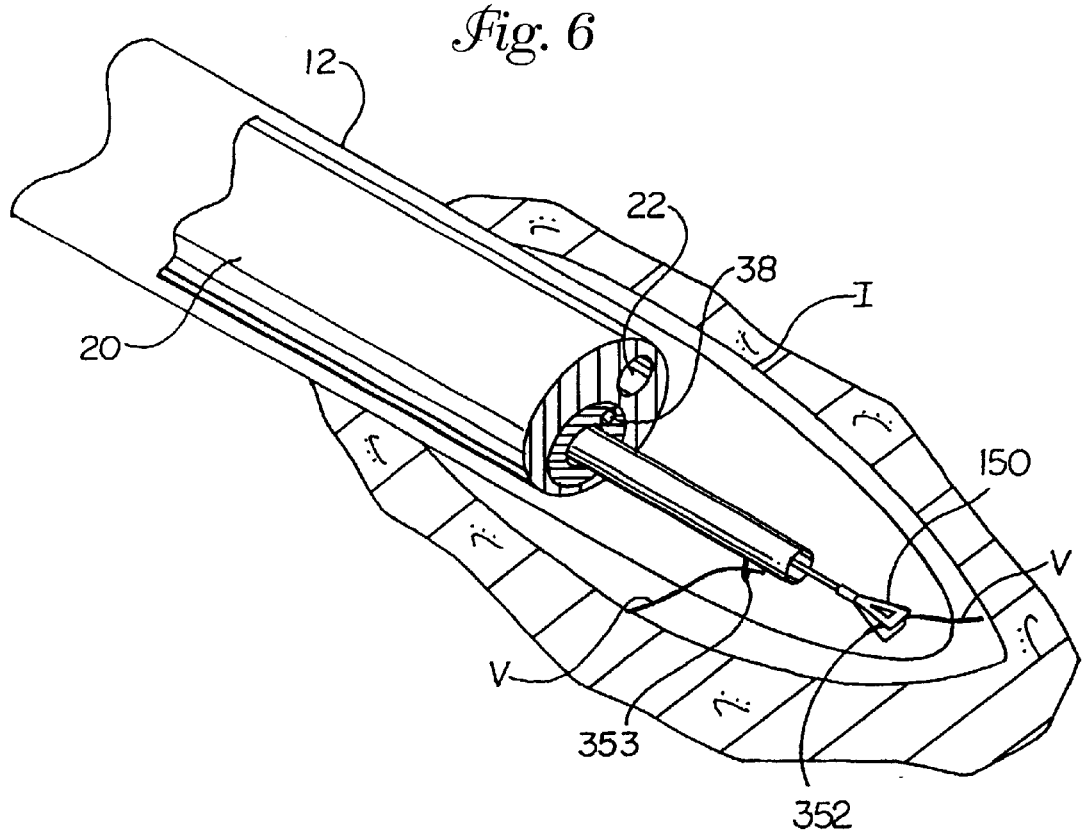
FIGS. 6 and 7 are enlarged perspective illustrations showing the distal end of the system in use during the harvesting of a blood vessel.

Turning now to the figures, the components of the vein harvesting system are illustrated. FIG. 1A shows device 10 comprising nonplanar housing 12 and removable (lower) portion 14. Housing 12 has an elongate shape defining a longitudinal axis. An arcuate tubular shape is shown in the drawings although it will be appreciated that other shapes could be used. FIG. 1B shows a bottom view of distal end 16 of device 10. As best seen in FIG. 1C removable portion 14 is held in position in housing 12 by slots 13a and 13b which extend longitudinally, nearly to distal end 16, through housing 12. Removable portion 14 preferably extends from proximal end 17 of device 10 to near distal end 16. Device 10 is inserted into an incision in the patient's leg (as illustrated in FIG. 6). The proximal end of device 10 remains outside of the incision and the physician grasps and removes removable portion 14. A cavity, space, or tunnel is thus created, permitting the insertion of tools for harvesting the vein. The housing is shaped and configured not only for insertion of tools, but for ease of insertion into the incision. It should be understood that additional means for creating a working space above the vein are also contemplated within the scope of this invention. For example, the device could comprise a unitary housing having a first profile upon insertion adjacent the vein and opening to a second profile once positioned. The opening from the first profile to the second profile creating a working space adjacent the vein. Such a configuration is disclosed in commonly assigned, co-pending application Ser. No. 09/715,382, filed on even date herewith, entitled "Vein Harvesting System and Method", the entirety of which is incorporated herein by reference.

In a preferred embodiment, a body portion having at least one lumen is used with the device. After removable portion 14 is removed, a body portion can be inserted into the housing and used with various tools to harvest the vein. Use of a body portion is preferred in order to protect the vessel from potential damage during the harvesting procedure. In a more preferred embodiment, the device is used with a multi-lumen body portion. The multi-lumen body portion is configured to be used in conjunction with one or more tools.

Various multi-lumen endoscopes and similar devices have been described in the art and may be useful with the device of this invention. For example, an endoscope configured to be used with various tools in harvesting blood vessels is described in U.S. Pat. No. RE 36,043 (Knighton), incorporated herein by reference in its entirety. U.S. Pat. No. 5,772,576 (Knighton et al.), also incorporated herein by reference in its entirety, describes a multi-lumen body portion capable of isolating the blood vessel from the tools used for removal of a blood vessel.

Figure 2A:
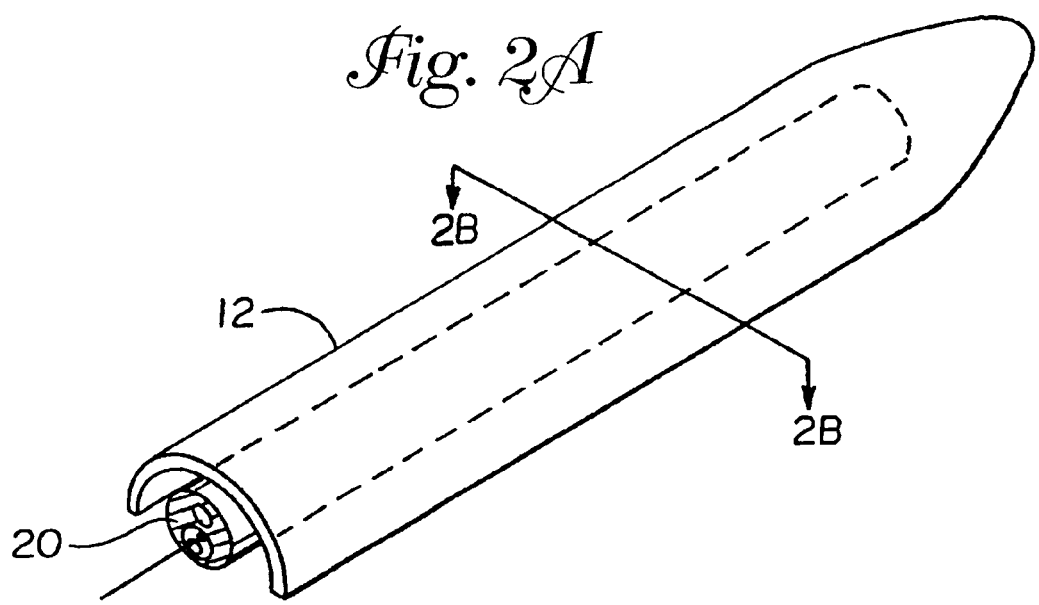
FIG. 2A is a perspective view of the housing of FIG. 1A containing a body portion.
Figure 2B:
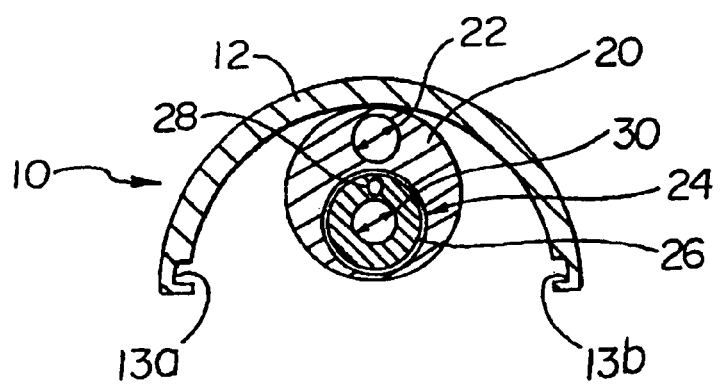
FIG. 2B is a transverse cross-sectional view of a preferred embodiment of the present invention, along line 2—2 of FIG. 2A.

FIG. 6 illustrates the position of preferred multi-lumen body portion 20 within the space created by housing 12 when the system is in use for vein harvesting. FIGS. 2A and 2B show housing 12 and multi-lumen body portion 20 in detail.

The components of preferred multi-lumen body portion 20 are shown in FIG. 2B in a transverse cross-sectional view, taken along line 2—2 of FIG. 2A. Multi-lumen body portion 20 is positioned within housing 12 and has two lumens, 22 and 24 extending longitudinally therethrough. Lumen 22 is configured to accept scissors, preferably bipolar scissors, and lumen 24 is configured to receive rotatable tube 26, itself comprising two lumens 28 and 30. The lumens extend longitudinally throughout body portion 20. Tube 26 freely rotates within lumen 24. Lumen 28 is configured to receive an optical fiber device or endoscope and lumen 30 is configured to receive a gripping tool, as described further below. In the embodiment illustrated in FIG. 2B, the lumens are generally circular in cross-section although they may be any shape suitable for the insertion of the tools.

Device 10 (i.e., housing 12 and removable portion 14) and multi-lumen body portion 20 may be constructed of a rigid material such as metal or plastic.

In the method of this invention, an incision is made in the area from which the vein is to be harvested. For example, the incision is made in the groin area for harvesting the saphenous vein. Another incision can be made near the knee if a long section of vein is needed. Device 10 is inserted through the incision and positioned over the top of the saphenous vein. Removable portion 14 is withdrawn from housing 12, leaving housing 12 in place over the vein, forming a workspace or tunnel. This workspace is now ready to receive tools, a body portion having at least one lumen, or, preferably, a multi-lumen body portion and associated tools and components, such as viewing devices.

The blood vessel (e.g., the saphenous vein) is cut and the end of the vessel is held by means of a gripping tool and pulled into vein dissecting lumen 30, as described further below.

Figure 4:
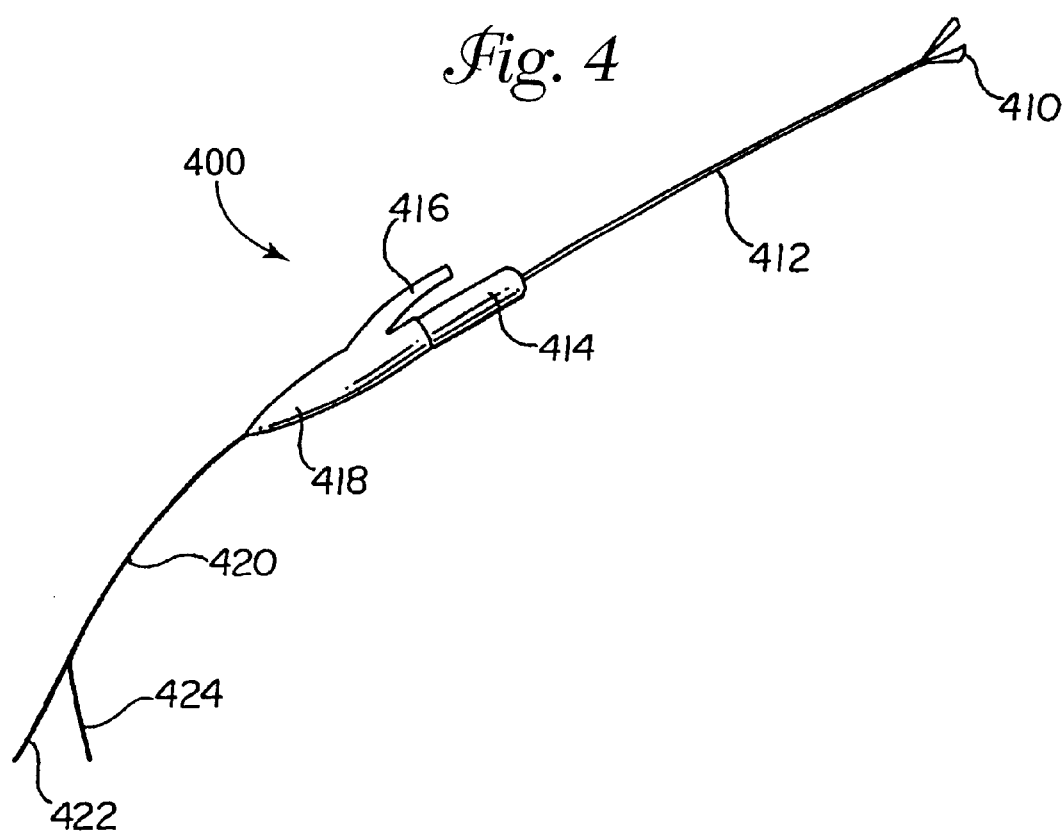
FIG. 4 is a side elevational view of bipolar scissors for use with the present invention.

The blood vessel is protected from damage by multi-lumen body portion 20 which isolates the vessel from the tools used to harvest the vessel. In addition, there is room to operate tools and remove the vessel without causing damage because of the workspace created by upper portion 16 of housing 12. A viewing device, such as an endoscope, is used so that the vein and side branches of the vein can be seen and cut. Preferably, these side branches are cut and cauterized with bipolar scissors (such as illustrated in FIG. 4), inserted through scissors lumen 22 of multi-lumen body portion 20.

Alternatively, side branches can be cut with scissors and ligated with a clip, which serves the same function as cauterization. The advantage to the use of bipolar scissors is that cutting and cauterizing of the side branches occurs in one step.

Lumen 30 (in rotatable tube 26) is of a size large enough to accommodate the blood vessel that is to be harvested as well as gripping tool 150. Rotatable tube 26 is inserted into lumen 24 of multi-lumen body portion 20. Gripping tool 150 is inserted into lumen 30 of rotatable tube 26 and the entire multi-lumen body portion 20 is moved distally until a desired length of vein is dissected. The distal end of the vein is cut, preferably with bipolar scissors, that are inserted into lumen 22 of multi-lumen body portion 20. The section of vein is then removed through lumen 30.

A second incision can be made below the knee and the process repeated if a longer piece of vein is needed.

Figure 5:
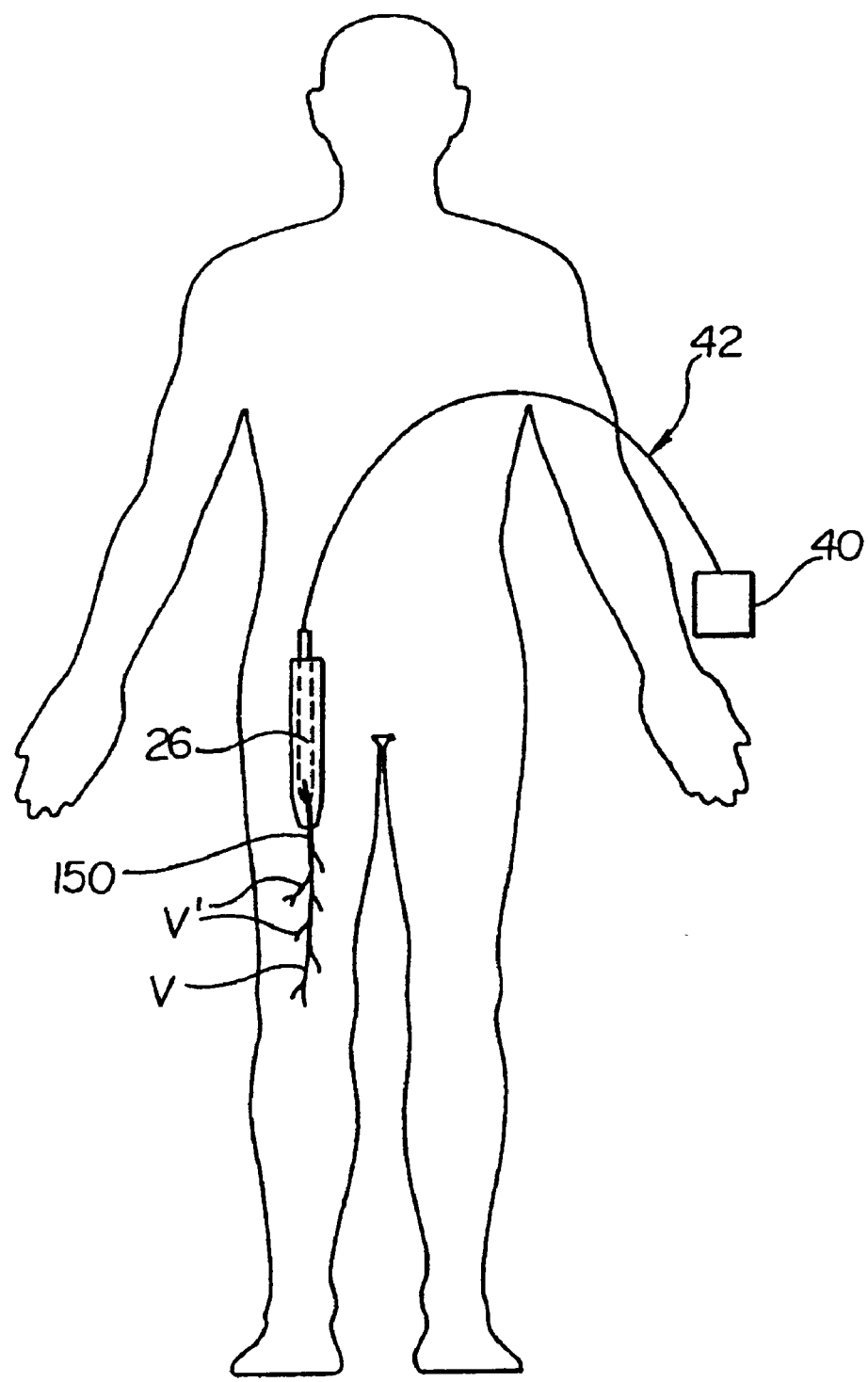
FIG. 5 is a schematic view of the vein harvesting device of the present invention being used in the removal of the saphenous vein of a patient.

Multi-lumen body portion 20 also has lumen 28, sized to accommodate a fiber optics viewing device 38 which includes an appropriate fiber optics illumination source, as illustrated in FIGS. 5 and 6. Device 38 is positioned such that the area immediately adjacent the distal end of body portion 20 can be illuminated and viewed by the operator. Device 38 is operably connected to an external monitor 40 that includes a suitable light source by conduit 42. Conduit 42 enters the endoscope lumen at endoscope port 28 of rotatable tube 26 (as shown in FIG. 2B). Multi-lumen body portion 20 could also be provided with an irrigation channel and/or a smoke evacuation channel if deemed necessary.

TOOLS

Figure 3:
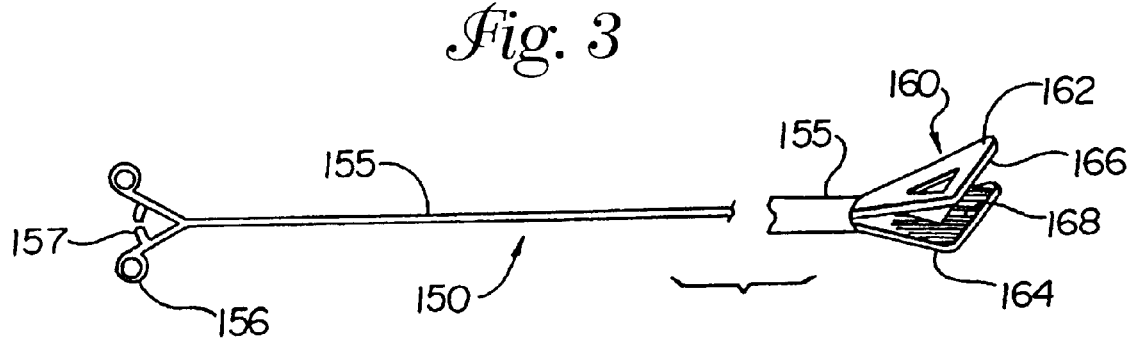
FIG. 3 is a side elevational view of a gripping tool for use with the present invention.

Gripping tool 150 in FIG. 3 is used to hold and retain the vessel being harvested. Gripping tool 150 has an elongated shaft 155, with handle 156 attached to a proximal end of shaft 155 and gripping mechanism 160 attached to a distal end of shaft 155. Handle 156 is preferably a scissors-type handle to actuate gripping mechanism 160 at the distal end of shaft 155 and includes latching mechanism 157 which allows the gripping mechanism to be locked in a set position (e.g., in a gripping position). Shaft 155 transmits the actuating movement from handle 156 to gripping mechanism 160. Gripping mechanism 160 includes first jaw 162 and second jaw 164 that oppose each other. When gripping handle 156 is operated by the physician, first jaw 162 and second jaw 164 are moved toward each other and may be used to grip blood vessel 20 between gripping surfaces 166 and 168. Jaws 162 and 164 are small enough to fit through lumen 30 of rotating tube 26.

During the entire procedure, the blood vessel is held in tension by the physician via gripping tool 150. Multi-lumen body portion 20 is advanced distally into the patient's body and the blood vessel is moved into lumen 30 of multi-lumen body portion 20, thus dissecting the blood vessel.

When a side branch is encountered during a vein dissection, bipolar scissors are inserted to cut and cauterize the side branch. Preferred bipolar scissors 400 are illustrated in FIG. 4. Blades 410 are positioned at the end of shaft 412. Shaft 412 can be turned by turning knob 414 in order to position the blades at the desired location. Handle 418 is connected to shaft 412 and provided with lever 416. Lever 416 is depressed to close blades 410. Handle 418 is connected to power cord 420 that has bipolar connectors 422 and 424. During use, the connectors preferably are activated by a foot switch (not shown) that is depressed to activate current flow to the blades (thus cauterizing the side branches) at the desired site.

Method of Operation

The vein harvesting device 10, multi-lumen body portion 20 and accompanying tools 150, 300 and 400 are used in combination for harvesting a vessel. After proper preparation of the incision site, the physician makes a small incision I (e.g., about 3 cm long) over the proximal aspect of the blood vessel to be harvested (as illustrated in FIGS. 5 and 6). Device 10, with removable portion 14 in place, is inserted into incision I and moved distally. After insertion to the desired position, removable portion 14 is removed and housing 12 is left in place, forming a workspace for the insertion of tools. As seen in FIG. 6, blood vessel V is then severed to expose free end 352 and free end 353 (which may be clipped as shown in FIG. 6). Free end 352 is grasped by gripping tool 150 which extends through lumen 30. Rotatable tube 26 is then moved down the vessel to dissect it from surrounding tissue. This is done for a short length under direct vision. For example, to remove a saphenous vein, an incision will be made at the groin over the saphenous vein and the vein will be dissected free from the junction of the common femoral vein. As shown in FIGS. 5 and 6, gripping tool 150 is inserted through lumen 30 of tube 26 such that the distal end of gripping tool 150 extends beyond the distal end of lumen 30. Free end 352 of blood vessel V is held by gripping tool 150 such that it is held under tension in the manner previously described. Rotatable tube 26 is then advanced distally over gripping tool 150 and blood vessel V is dissected away from surrounding connective tissue. Side branches V' are cut (and cauterized) as necessary during the dissection.

Figure 7:
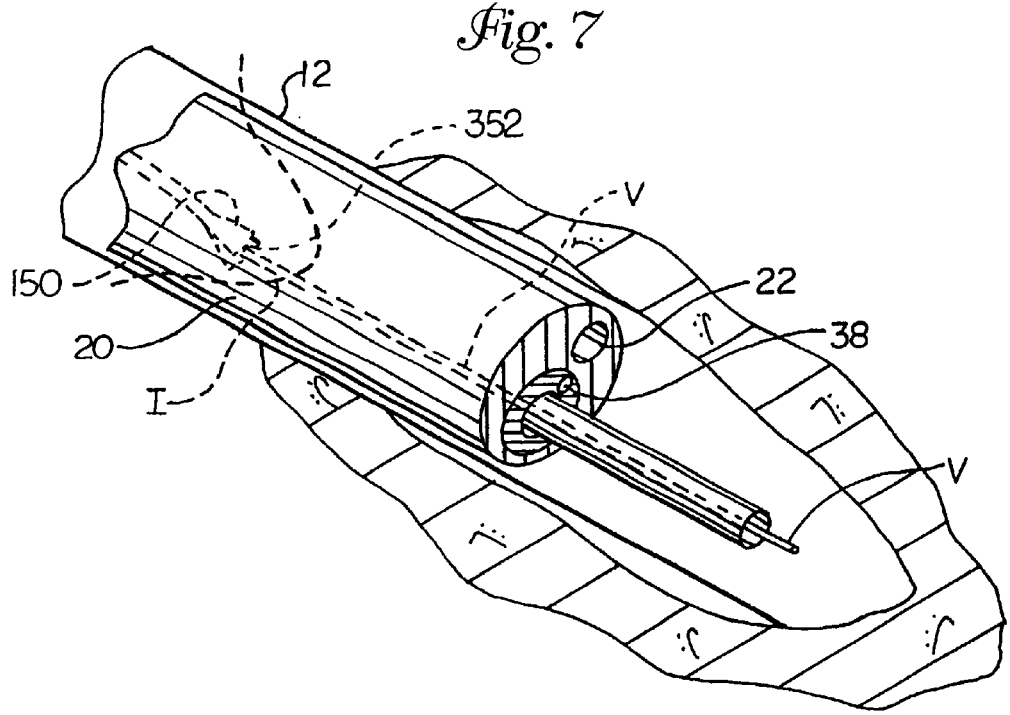

As illustrated in FIG. 7, the dissection process proceeds distally along blood vessel V. The patient's body is not shown in order to show the harvesting system in operation, and incision I is indicated by a dotted line. Multi-lumen body portion 20 is advanced along with the rotatable tube 26 into the incision. Gripping tool 150 continues to grasp the vein. Until this point, the operator has been viewing the procedure under direct vision. Now, the operator switches to viewing the dissection process (occurring at the area immediately adjacent the distal end of the lumen 24) through the fiber optic viewing device 38 located at the distal end multi-lumen body portion 20. Viewing device 38 is positioned in lumen 28 of rotatable tube 26. Alternatively, the viewing device could be provided by a separate scope. As previously discussed, viewing device 38 provides adequate lighting for the operator to view the dissection and tool operations occurring within the patient via the monitor. Irrigant may be introduced as necessary through an irrigation channel (not shown) to keep blood or other body tissue from obscuring vision adjacent the distal end of multi-lumen body portion 20.

During the dissection process, bipolar scissors 400 are used as needed to cut and cauterize side branches V'. Typically, the bipolar scissors remain in lumen 22 and are advanced (to expose and use the blades) when needed. The dissection proceeds until a desired length of vein is cut. The maximum length of the vein typically is limited by the length from the incision near the groin to the knee. The vein is then removed through the proximal end of lumen 30, though the entire multi-lumen body portion could be removed proximally with the vein in lumen 30.

The harvested blood vessel is then ready for use in, for example, coronary bypass surgery.

Although particular embodiments have been disclosed herein in detail, this has been done for purposes of illustration only, and is not intended to be limiting with respect to the scope of the claims. In particular, it is contemplated that various substitutions, alterations, and modifications may be made to the invention without departing from the spirit and scope of the invention as defined by the claims.

What is claimed is:

1. A method of removing a section of a generally cylindrical tissue structure from the body of a human or animal comprising:

provide a device having a first portion and a second portion, the first portion having a non-planar shape and the second portion being substantially planar, the first and second portions defining a working space there between, the second portion being movable with respect to the first portion;

exposing a proximal end of the tissue structure section to be harvested through an incision in the body;

inserting the device through the incision such that the second portion is positioned between the first portion and the tissue structure;

moving the second portion with respect to the first portion to expose the working space between the first portion and the tissue structure;

inserting at least one tool through the incision into the working space;

dissecting the tissue structure away from surrounding tissue with the at least one tool;

cutting a proximal end of the tissue structure section;

cutting a distal end of the tissue structure section; and removing the tissue structure section through the incision.

2. The method of claim 1 wherein the step of providing a device includes providing a device wherein the second portion is slidably engaged to the second portion and wherein the step of moving the second portion with respect to the first portion includes sliding the second portion out of engagement with the first portion.

3. A system for removing a generally cylindrical tissue structure from a human or animal body comprising:

a device having an elongate nonplanar housing defining a longitudinal axis;

a substantially planar movable portion configured to be movable with respect to the housing from an engaged position where an at least partially enclosed working space is defined between the housing and the movable portion and a working position where the working space is exposed, the housing and movable portion being sized to be insertable through the incision and positioned adjacent the tissue structure; and at least one tool used in removing the tissue structure, the tool having a distal operative tip and being sized to be accommodated within the working space.

4. The system of claim 3 further comprising an elongate element having a first lumen sized for accommodating the tissue structure and a second lumen sized for accommodating at least one tool.

5. A method for creating a working space for at least one tool over a generally cylindrical tissue structure in a human or animal body comprising:

providing a device having a first portion and a second portion, the first portion having a non-planar shape and the second portion being substantially planar, the first and second portions defining a working space there between, the second portion being movable with respect to the first portion;

making an incision in the body above the tissue structure;

inserting the device through the incision such that the second portion is positioned between the first portion and the tissue structure;

moving the second portion with respect to the first portion to expose the working space between the first portion and the tissue structure; and inserting the at least one tool through the incision into the working space.

6. A device for insertion through an incision for creating a working space for at least one tool adjacent a generally cylindrical tissue structure in a human or animal body comprising:

an elongate nonplanar housing defining a longitudinal axis;

a substantially planar movable portion configured to be movable with respect to the housing from an engaged position where an at least partially enclosed working space is defined between the housing and the movable portion and a working position where the working space is exposed, the housing and movable portion being sized to be insertable through the incision and positioned adjacent the tissue structure.

* * * * *